United States Patent
Wicky

(10) Patent No.: US 7,497,135 B2
(45) Date of Patent: Mar. 3, 2009

(54) METHOD FOR PLACING A RECEPTACLE CONTAINING A LIQUID IN A DEVICE FOR SAMPLING THE LIQUID AND SAMPLING DEVICE FOR APPLYING THE METHOD

(75) Inventor: Andre Wicky, Cudrefin (CH)

(73) Assignee: Biomerieux, Marcy l'Etoile (FR)

( * ) Notice: Subject to any disclaimer, the term of this patent is extended or adjusted under 35 U.S.C. 154(b) by 415 days.

(21) Appl. No.: 10/557,176

(22) PCT Filed: May 19, 2004

(86) PCT No.: PCT/FR2004/050203

§ 371 (c)(1),
(2), (4) Date: Nov. 17, 2005

(87) PCT Pub. No.: WO2004/109296

PCT Pub. Date: Dec. 16, 2004

(65) Prior Publication Data

US 2006/0254370 A1   Nov. 16, 2006

(30) Foreign Application Priority Data

May 28, 2003   (FR) .................................. 03 06474

(51) Int. Cl.
*G01N 35/10* (2006.01)
(52) U.S. Cl. .................. 73/864.25; 73/864.21
(58) Field of Classification Search .............. 73/864.21, 73/864.25
See application file for complete search history.

(56) References Cited

U.S. PATENT DOCUMENTS

| | | | | |
|---|---|---|---|---|
| 3,230,776 A | * | 1/1966 | Isreeli et al. .............. | 73/864.25 |
| 3,252,330 A | * | 5/1966 | Kling ................... | 73/864.25 X |
| 3,282,651 A | * | 11/1966 | Ferrari et al. ......... | 73/864.21 X |
| 3,529,475 A | * | 9/1970 | Muhlestein et al. ... | 73/864.21 X |
| 3,544,272 A | * | 12/1970 | Vaills ................... | 73/864.25 X |
| 3,853,008 A | * | 12/1974 | Hoffa et al. ........... | 73/864.25 X |
| 3,858,450 A | * | 1/1975 | Jones ................... | 73/864.21 X |
| 3,949,615 A | * | 4/1976 | Stein et al. ............ | 73/864.25 X |
| 4,343,766 A | * | 8/1982 | Sisti et al. ............. | 73/864.21 X |

(Continued)

FOREIGN PATENT DOCUMENTS

EP   0 837 331 A1   4/1998

(Continued)

*Primary Examiner*—Thomas P Noland
(74) *Attorney, Agent, or Firm*—Oliff & Berridge, PLC

(57) ABSTRACT

A method for placing a receptacle in a device for sampling liquid is described. It utilizes a device for sampling a liquid present in the receptacle, enabling the method of placing said receptacle to be applied. This method includes placing the receptacle, such as a bottle, having an opening and containing a liquid of interest, in a device for sampling the liquid. The sampling device having a sampling needle. The method further includes a linear movement of the receptacle and a simultaneous pivoting movement of the needle, during which movements the free end of said needle is moved between a terminal position outside said receptacle and a terminal position inside it. The longitudinal axis of the needle and the perpendicular plane of the opening forming a substantially constant intersection during the placing of the receptacle. The preferred industrial application of the invention is to the field of in vitro diagnosis.

16 Claims, 7 Drawing Sheets

U.S. PATENT DOCUMENTS

| | | | |
|---|---|---|---|
| 4,478,095 A | 10/1984 | Bradley et al. | 73/864.21 |
| 4,570,495 A | 2/1986 | Terada | 73/864.25 |
| 5,015,591 A * | 5/1991 | Meyrat et al. | 73/864.25 X |
| 5,084,242 A | 1/1992 | Sakuma et al. | 422/100 |
| 5,171,527 A * | 12/1992 | Knippscheer et al. | 73/864.25 X |
| 5,744,729 A | 4/1998 | Tanaka | 73/864.25 |
| 5,913,237 A | 6/1999 | Gysi | 73/41 |
| 6,958,130 B1 * | 10/2005 | Gicquel et al. | 422/65 |
| 7,097,981 B1 * | 8/2006 | Gicquel et al. | 435/7.1 |

FOREIGN PATENT DOCUMENTS

| | | |
|---|---|---|
| JP | A 03-202772 | 9/1991 |
| WO | WO 93/21534 A1 | 10/1993 |
| WO | WO 96/07918 A1 | 3/1996 |
| WO | WO 00/16075 A1 | 3/2000 |
| WO | WO 03/059515 A2 | 7/2003 |

* cited by examiner

METHOD FOR PLACING A RECEPTACLE CONTAINING A LIQUID IN A DEVICE FOR SAMPLING THE LIQUID AND SAMPLING DEVICE FOR APPLYING THE METHOD

BACKGROUND

The present invention relates to a method for placing a receptacle, such as a bottle containing a liquid of interest, in a device for sampling the liquid. It also relates to a sampling device for the application of the placing method.

This invention is particularly useful for receptacles containing liquid samples which may be dangerous, such as:
   biological substances,
   marking substances (fluorescent, chromogenic, radioactive, etc.) which may be associated with biological substances,
   rinsing solutions,
   magnetic particles in solution.

Such recipients are generally used in automatic in vitro diagnostic systems for analyzing various parameters or biological substances which are intrinsically dangerous for the user, and may consist wholly or partially of:
   viruses (hepatitis B, hepatitis C, AIDS, etc.),
   pathogenic bacteria (*Staphylococcus aureus, Streptococcus pneumoniae,* etc.),
   antibodies or antigens,
   nucleic acid sequences (essentially RNA and DNA).

Such automatic systems are particularly clearly described in patent applications WO-A-00/16075 and EP-A-0 837 331. The prior art thus generally consists of receptacles in the form of bottles. These bottles are positioned vertically, in such a way that it is difficult for the sampling means to recover all the liquid of interest contained in each bottle. This quantity of liquid which remains in the bottle is therefore a source of potential contamination for the use of the automatic diagnostic system equipped in this way. Furthermore, said user is obliged to move each receptacle into place until the sampling means associated with it are properly positioned; to achieve this, it is generally necessary to snap or screw each bottle into place with respect to the device for sampling said liquid of interest, which may give rise to splashes which are also a source of contamination.

The object of the present invention is to respond to the drawbacks of the prior art as described above, by proposing a placing method and a device for applying this method which are simple and can easily be automated, but which, when said device is manual, considerably reduce the risks of contamination for the user.

SUMMARY

The invention therefore relates to a method for placing a receptacle, such as a bottle having an opening and containing a liquid of interest, in a device for sampling the liquid, the sampling device having a sampling needle, the method comprising a linear movement of the receptacle and a simultaneous pivoting movement of the needle, during which movements the free end of said needle is moved between an extreme position outside said receptacle and an extreme position inside it, the longitudinal axis of the needle and the perpendicular plane of the opening forming a substantially constant intersection during the placing of the receptacle.

The phrase "perpendicular plane of the opening" denotes the plane perpendicular to the longitudinal axis of the receptacle positioned at the level of the opening of the receptacle.

The phrase "substantially constant intersection" denotes that the intersection between the perpendicular plane of the opening and the longitudinal axis of the needle is always located between the walls of the receptacle which form its opening, but without touching said walls.

In a particularly useful embodiment, the pivoting of the needle takes place in a plane containing the linear axis of movement of the receptacle.

In another particularly useful embodiment, the general movement of the receptacle is an upward movement, while the general movement of the needle is a downward movement.

Also in a particularly useful embodiment, in the extreme inner position of the needle, the free end of said needle is located substantially in the lowest point of the receptacle, with respect to the earth's gravity.

The present invention also proposes a device for sampling a liquid present in a receptacle, permitting the application of the receptacle placing method, as described above, the device comprising:
   a sampling needle, mounted on a pivoting support, and
   a carriage supporting the receptacle, this carriage being mounted on sliding means.

In a specific embodiment, the device includes transmission means which are present between the sliding means and the pivoting support, with the purpose of making the linear and pivoting movements simultaneous.

In a variant embodiment, the transmission means comprise at least one strip interacting with guide and hinge shafts, a chain, a belt and/or a pinion sequence.

Finally, in another embodiment, the sliding means comprise at least two rods which are parallel to each other and to the movement of the vessel when it is being placed.

In the remainder of the description, the phrase "generally upward movement" denotes a vertical or oblique movement from a low position towards a high position, the low and high positions being defined with respect to the Earth's gravity, the low position being closest to the ground and the high position being farthest from it. The phrase "generally downward movement" denotes a vertical or oblique movement from a high position towards a low position, the low and high positions being defined as above.

BRIEF DESCRIPTION OF THE DRAWINGS

The attached figures are provided by way of example to illustrate the present invention, and are not restrictive in nature.

Finally.

DETAILED DESCRIPTION OF EMBODIMENTS

Figure 1:
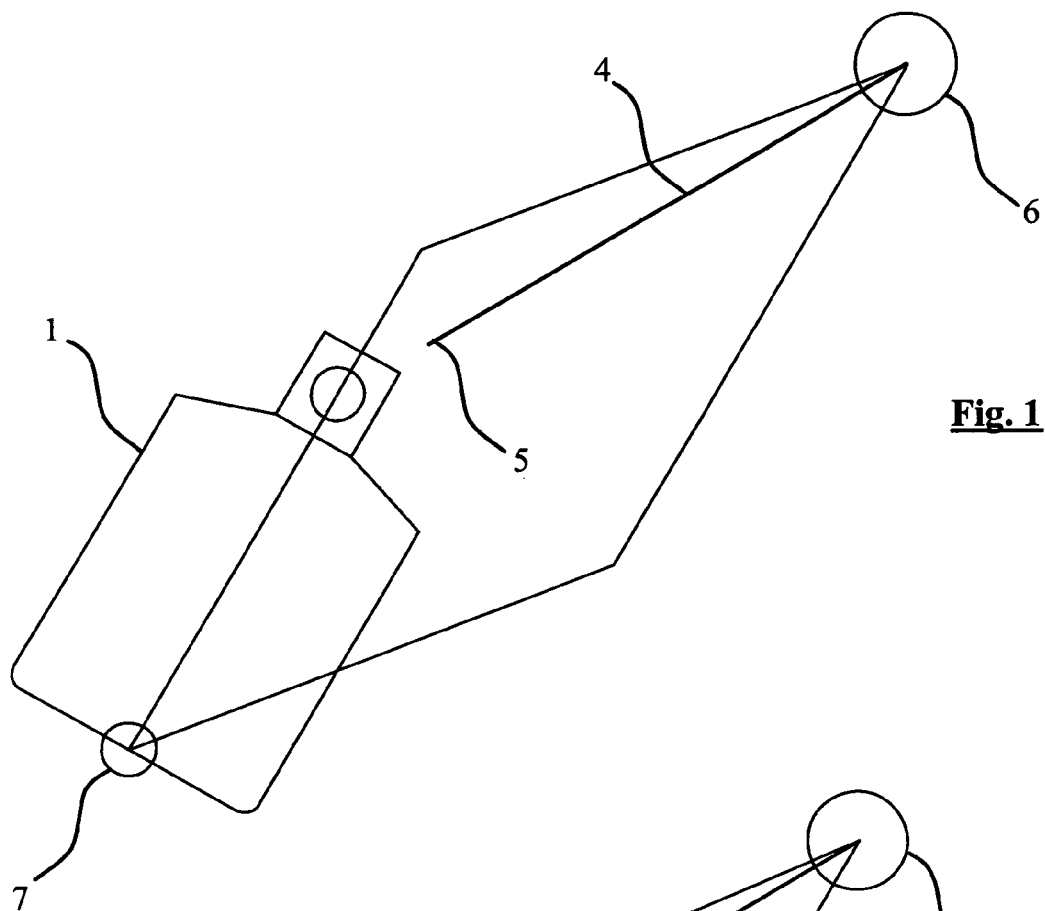
FIG. 1 shows a schematic view of the sequence of the placing method according to the invention, before the free end of the needle penetrates into the receptacle through its opening, as in the case of the extreme outer position.

The present invention relates to a method for placing a receptacle 1, this method being clearly shown in the set of FIGS. 1 to 9 of the present patent application. These figures show the whole of the sequence of the placing of the receptacle 1, with respect to a sampling device 4, represented here by a rigid sampling needle.

This method essentially consists in enabling the free end 5 of the needle 4 to be introduced through the opening 2 of the receptacle 1, without allowing any part of the needle 4 to touch the inner, or of course the outer, edges of said receptacle 1, either at the level of the opening 2 or in the rest of the receptacle 1. In all the figures, it should be noted that this receptacle 1 consists of a bottle 1. The only access to the inside of this bottle 1 is via an upper position at the level of the opening 2, when the bottle 1 is placed on its bottom.

It should also be noted that, in all of these figures, the bottle 1 approaches the pivoting support 6 without changing its inclination. It only undergoes a simple sliding movement.

In FIG. 1, the needle 4 has not yet been introduced into the bottle 1.

Figure 2:
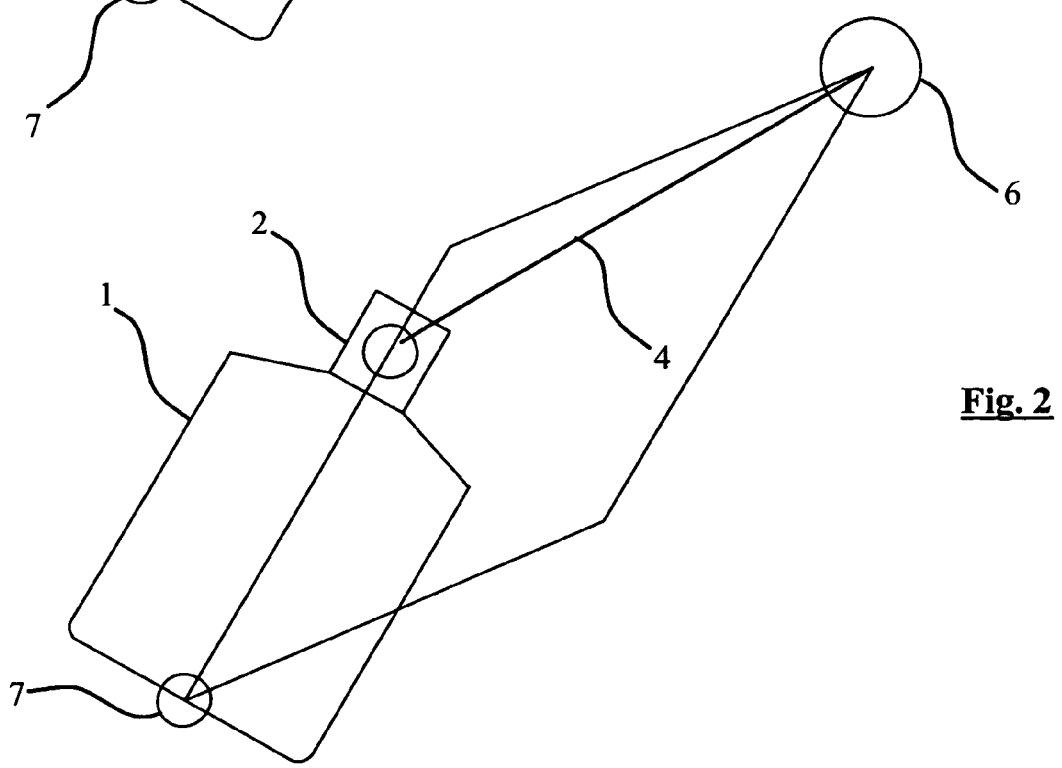
FIG. 2 shows a schematic view of the sequence of the placing method according to the invention, when the free end of the sampling needle is located at the level of the receptacle in its opening.

In FIG. 2, the introduction of the needle 4 is beginning to take place. The free end 5 is therefore at the level of the opening 2 of the receptacle 1.

Figure 3:
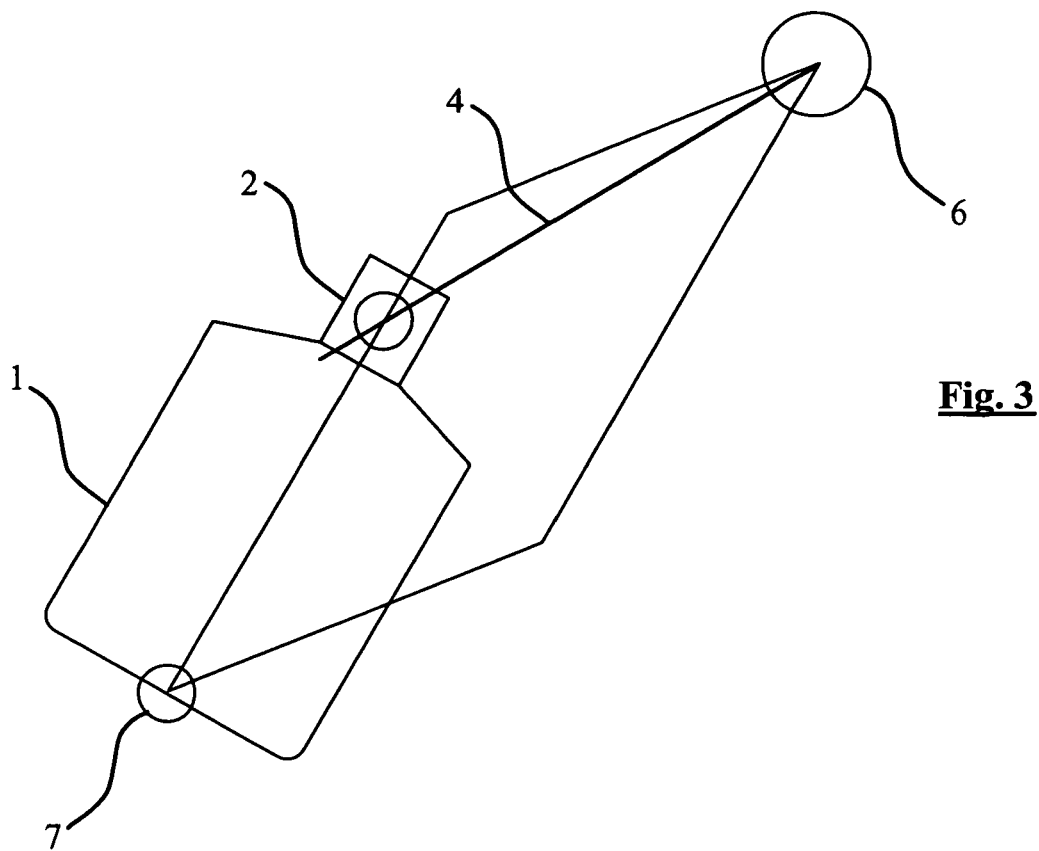
FIGS. 3 to 8 show schematic views of the sequence of the placing method according to the invention, when the free end of the sampling needle is located inside the receptacle.

In FIG. 3, while the needle continues to pivot, the free end 5 is inside the bottle 1. It remains there throughout the rest of the introduction sequence.

Figure 4:
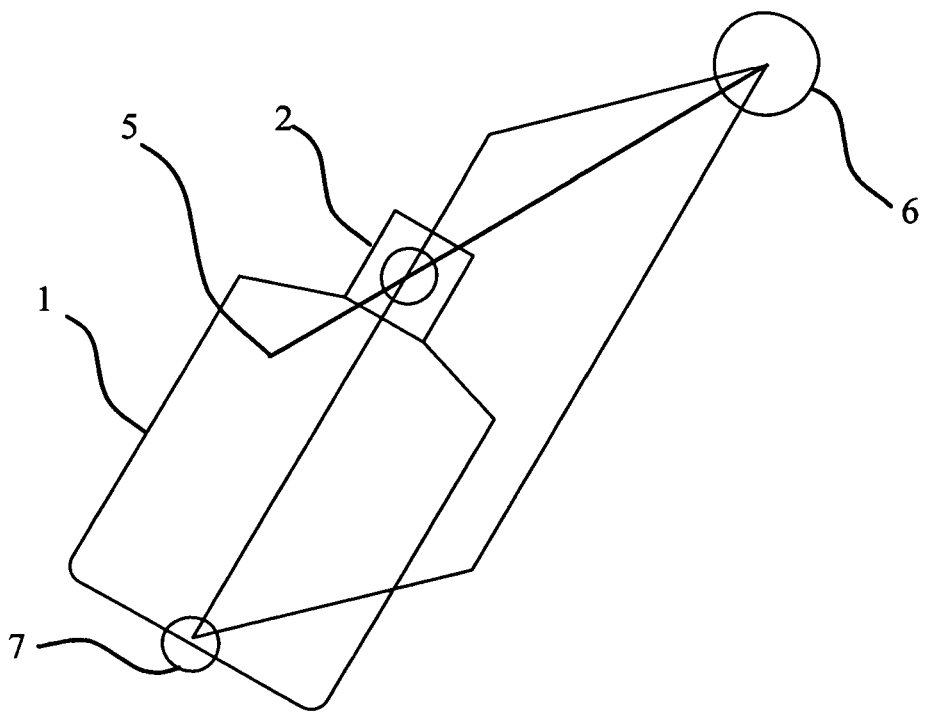
Figure 5:
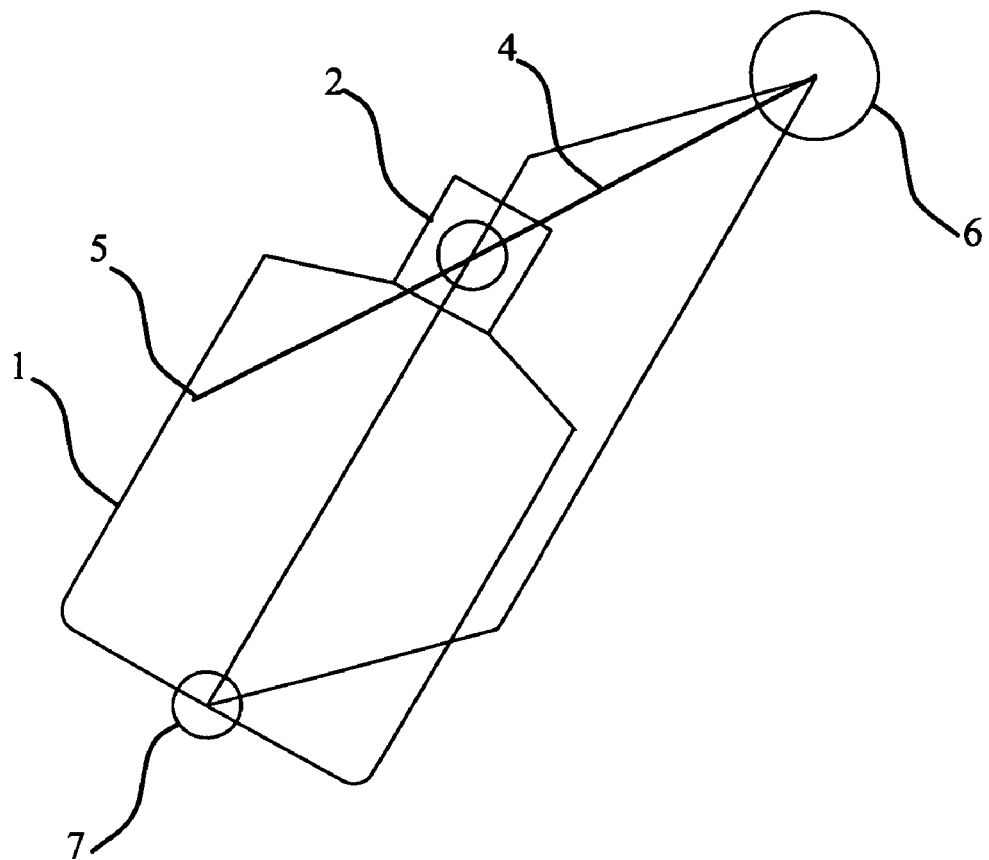
Figure 6:
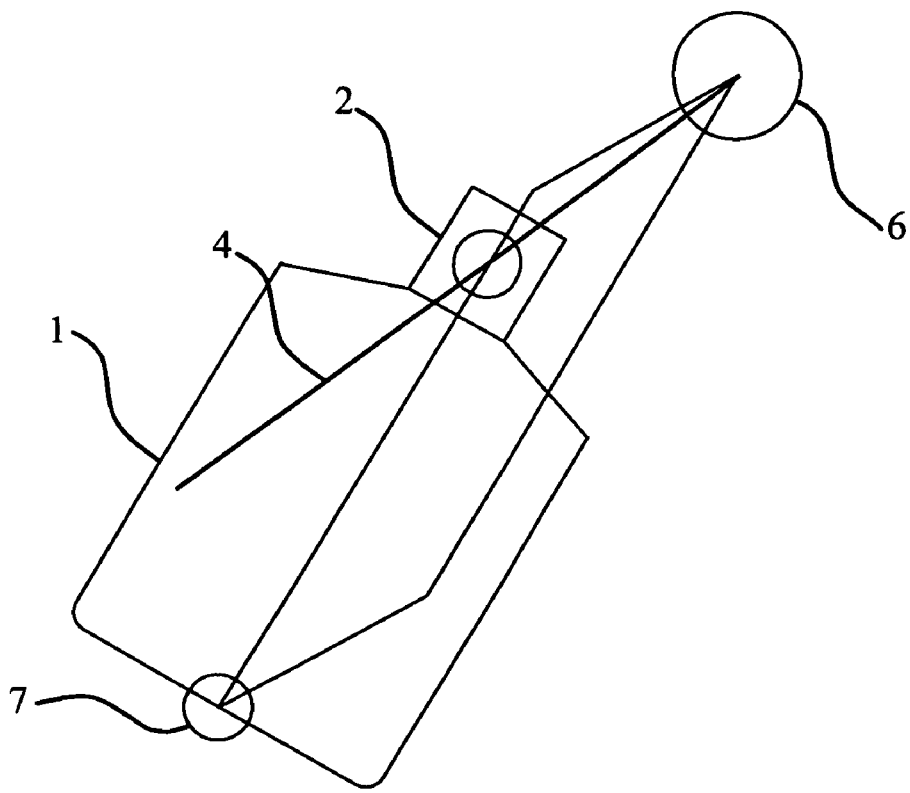
Figure 7:
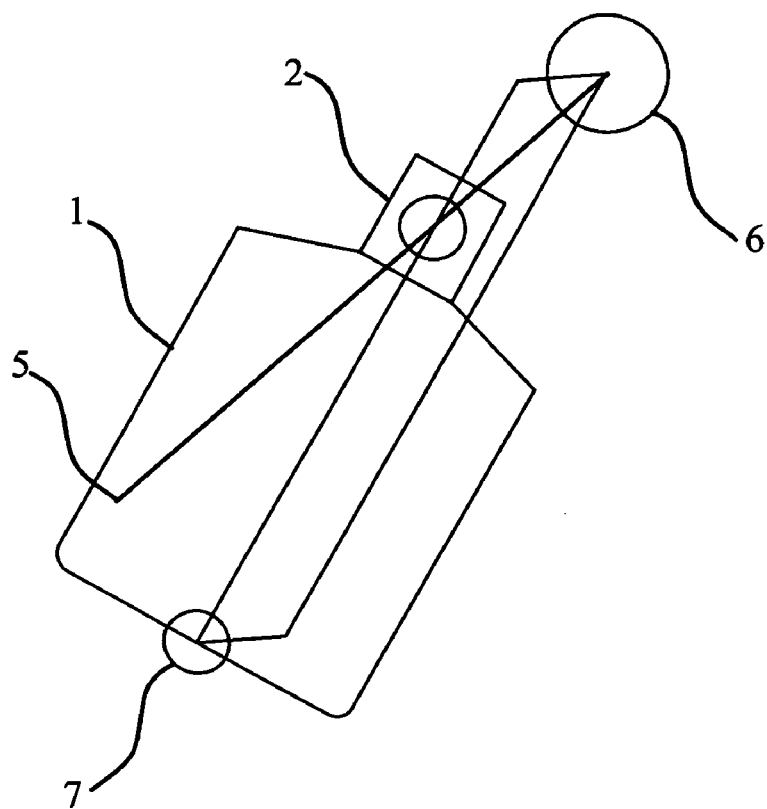
Figure 8:
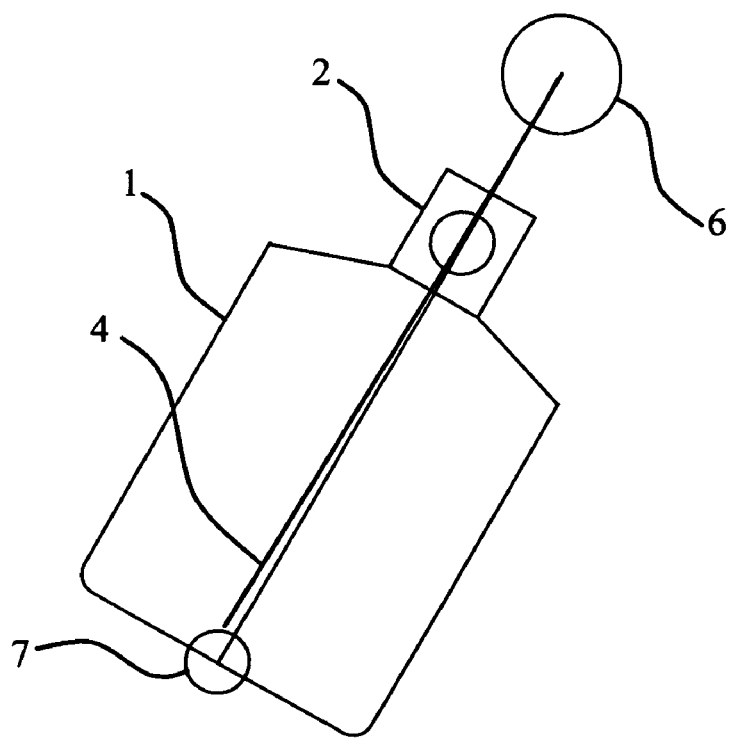

In FIG. 4, the pivoting of the needle 4 is accentuated, and consequently the free end 5 is even farther inside the receptacle 1.

FIGS. 5, 6, 7 and 8 are intermediate figures which show, chronologically, the pivoting of the needle 4 and the approach of the supporting carriage 7 to the pivoting support 6.

Figure 9:
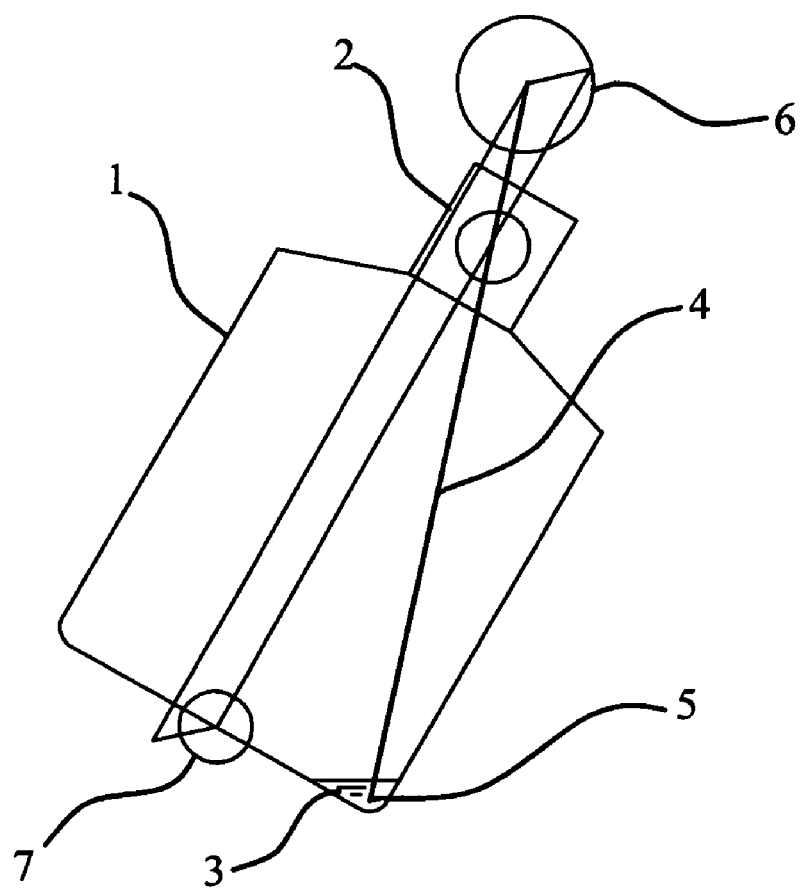
FIG. 9 shows a schematic view of the sequence of the placing method according to the invention, when the free end of the needle is located substantially at the lowest point of the receptacle with respect to the Earth's gravity, as in the case of the extreme inner position.

The final position is that shown in FIG. 9, where the free end 5 is located in the lowest position of the receptacle 1, in such a way that it is possible to extract virtually all of the liquid of interest 3 contained in said bottle 1. To facilitate the interpretation of FIGS. 1 to 8, this liquid 3 is only shown in FIG. 9. This facilitates the handling of the empty bottle 1, while safeguarding the user from any possible contamination by said liquid of interest.

Figure 10:
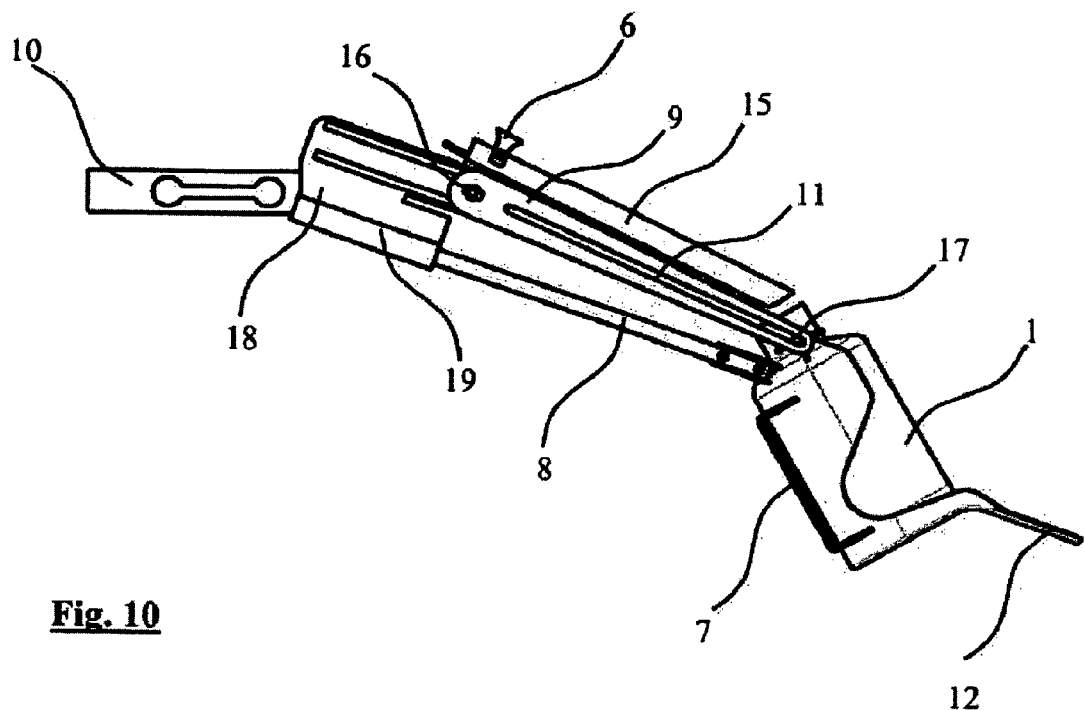
FIG. 10 shows a lateral view of the sampling device in the presence of the receptacle, in the position preceding the introduction of the sampling needle, showing the means of transmitting movements between the sliding carriage and the pivoting support.
Figure 11:
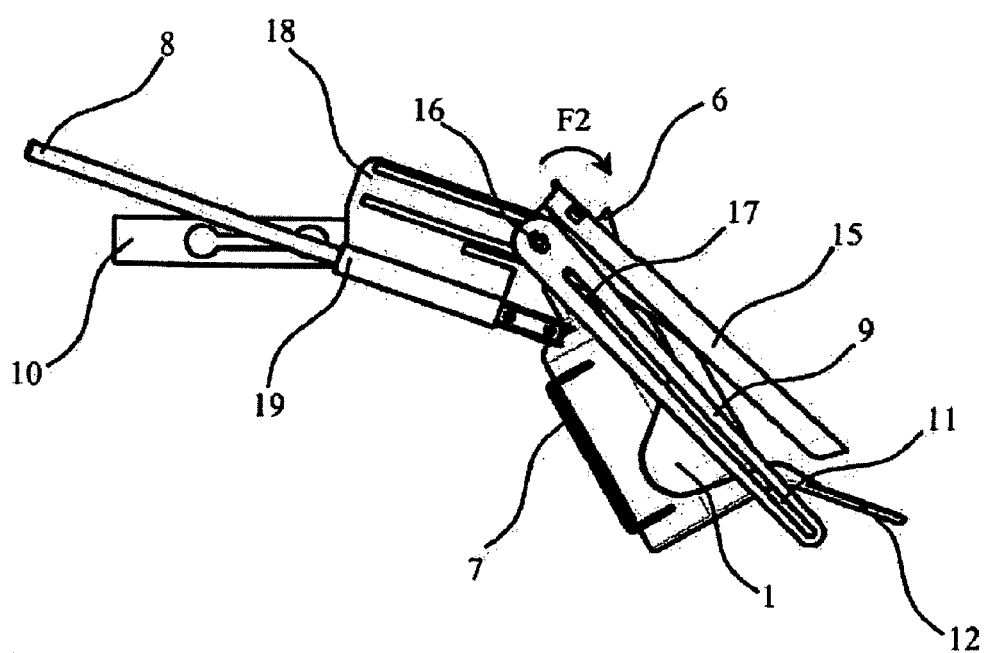
FIG. 11 shows a lateral view of the sampling device in the presence of the receptacle, in the position after the introduction of the sampling needle, showing the means of transmitting movements between the sliding carriage and the pivoting support.

FIGS. 10 and 11 show a lateral view of the carriage 7 supporting the receptacle 1 and a frame 18 supporting the sampling means 4, making apparent the means 9 for transmitting the movements between the pivoting support 6, in the direction F2 in FIG. 11, supporting the sampling needle 4 and the sliding carriage 7 supporting the receptacle 1. This is a view from the left-hand side, since, in the embodiment shown here, the transmission means 9 are present on this side only, although clearly it is possible for these means 9 to be present on the right-hand side or on both sides at once, in order to provide more balanced operation. Said transmission means 9 consist of:

a strip which has, on the one hand, a hinging axis 16 , and, on the other hand, a guide slot 11, and a guide axis 17 carried by the lateral support 14, at the level of the opening 2.

This guide axis 17 actually consists of a locating pin which is present and interacts with the slot 11. In a first extreme position, said axis 17 is placed at one of the ends of the slot 11 as shown in FIG. 10, while in a second extreme position the axis 17 is placed at the other end of the slot 11, as shown in FIG. 11.

Figure 12:
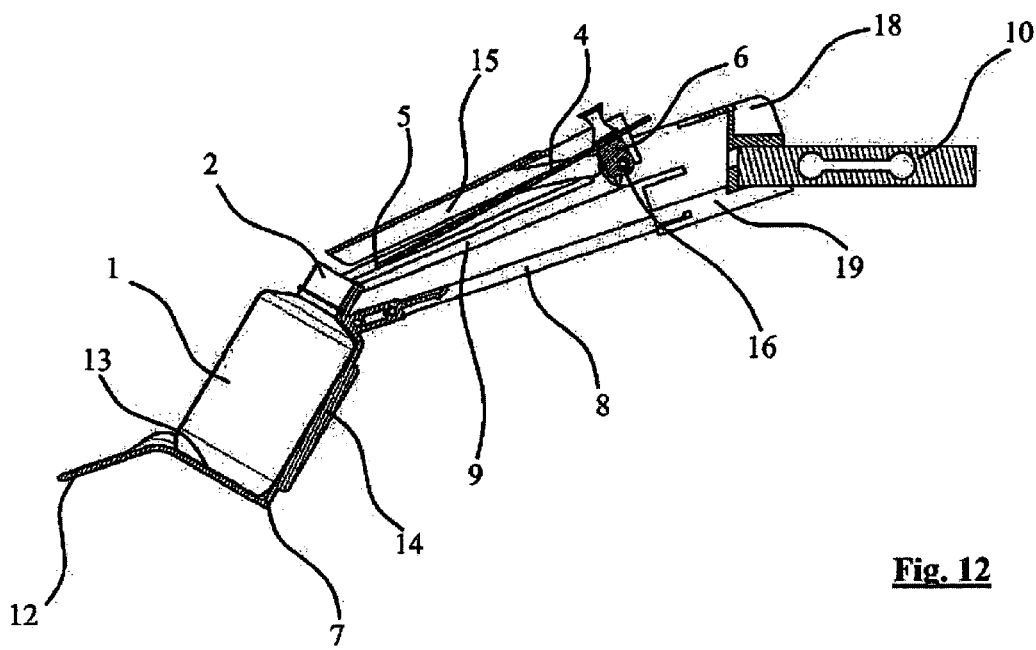
FIG. 12 shows a view in longitudinal section of the sampling device of FIG. 10 of the sampling device in the presence of the receptacle, before the free end of the sampling needle has penetrated into the receptacle through its opening, as in the case of the extreme outer position.
Figure 13:
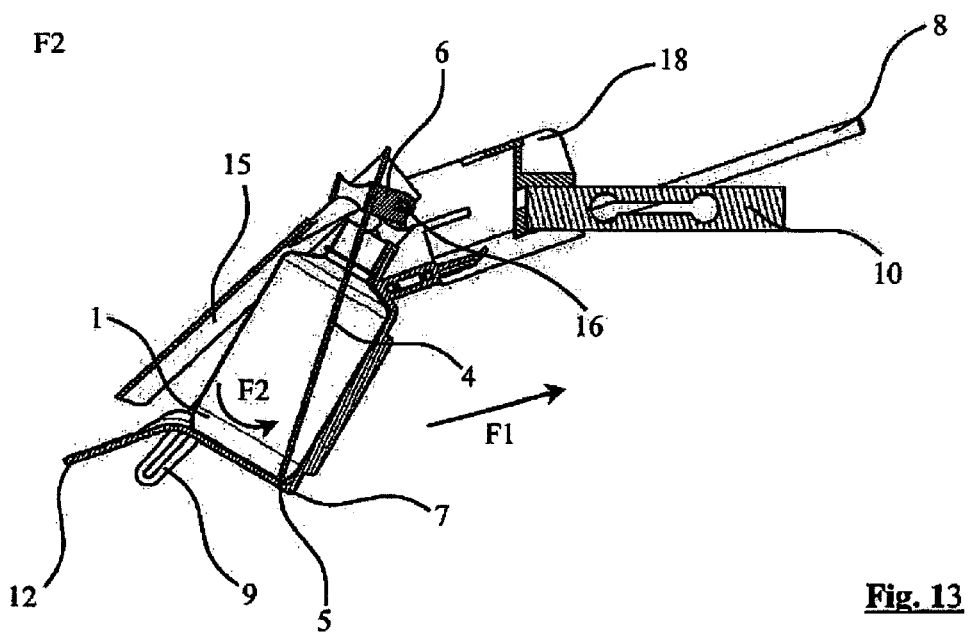
FIG. 13 shows a view in longitudinal section of the sampling device of FIG. 11, in other words when the free end of the sampling needle is located substantially at the lowest point of the receptacle, with respect to the Earth's gravity, as in the case of the extreme inner position.

Thus the user opens the top of the bottle 1 and positions said bottle 1 in its carriage 7, as shown in FIG. 10. Then, in order to make the bottle 1 approach the needle 4, he carries out a sliding movement in the direction F1, by acting on the handle 12 of the carriage 7, parallel to the longitudinal axis of the sliding means 8, in such a way that said means slide within the guides 19 fixed to the frame 18, as shown in FIGS. 12 and 13. This approach causes the guide axis 17 to slide inside the slot 11, in such a way that the transmission means 9 oscillate in the direction F2 to enable the needle 4 to be introduced into the bottle 1.

It should be noted that the frame 18 is fixed to the structure of the measuring instrument, not shown in the figures, by a support 10 which can contain a sensor for detecting the total weight of the sampling device 4, the carriage 7 and the bottle 1 with its contents 3. Since the only variable is the liquid 3, it is possible for the apparatus to inform the operator of the need to replace the empty bottle 1 with a full bottle 1. Sensors of this type are well known to those skilled in the art. This also permits the automation of the filling monitoring, this automation possibly being extended until sliding in the direction F1 is possible, this automation also being well-known to those skilled in the art.

FIGS. 12 and 13 show more precisely the whole of the sampling device 4 and the receptacle 1 in the extreme positions, in other words, on the one hand, before the needle 4 penetrates into the bottle 1, as shown in FIG. 12, and, on the other hand, when the needle 4 is in the position for sampling the liquid 3 contained in said bottle 1, as shown in FIG. 13.

It will be noted in these figures that the carriage 7 comprises a handle 12 for manipulating said carriage 7. This handle 12 has, among other features, a cavity 13 in which the bottom of the receptacle 1 can be placed. In this configuration, it is clear that the bottle 1 is correctly held in position, particularly since it will also be noted that a lateral support 14 is present and supports said bottle 1 laterally. For its part, the sampling device 4 is associated with the pivoting support 6 which comprises:

the hinge axis 16 which also serves for the pivoting of the transmission means 9, and an upper guard 15 which protects the user and/or the automatic diagnostic system from any contamination by the liquid contained in the bottle 1; this guard 15 is also mounted pivotably about said hinge axis 16.

Between the two extreme positions of the sampling needle 4, shown essentially in FIGS. 1 and 9, but also in FIGS. 10 and 11 and FIGS. 12 and 13, it is thus possible to note a linear sliding movement of the receptacle 1 in the direction F1 and a pivoting of the sampling device 4 in the direction F2, as shown more specifically in FIGS. 11 and 13.

It will also be noted in FIGS. 10 to 13 that the carriage 7 is movable along sliding means 8, consisting in the present case of two rods parallel to each other and located on either side of the receptacle 1.

REFERENCES

1. Receptacle, such as a bottle
2. Opening of the receptacle 1
3. Liquid of interest contained in the receptacle 1
4. Sampling device, such as a sampling needle
5. Free end of the needle 4
6. Pivoting support carrying the sampling needle 4
7. Carriage supporting the receptacle 1
8. Sliding means along which the carriage 7 can move
9. Transmission means present between the carriage 7 and the pivoting support 6
10. Support of the sampling device 4
11. Slot in the transmission means 9
12. Handle of the carriage 7
13. Cavity in the chariot 7 receiving the bottom of the receptacle 1
14. Lateral support of the receptacle 1
15. Guard for the introduction of the pivoting support 6 into the receptacle 1
16. Hinge axis of the support 6, the transmission means 9 and the guard 15
17. Guide axis carried by the lateral support 14, present at the level of the opening 2 and interacting with the slot 11
18. Frame supporting the sampling means 4
19. Guide carried by the frame
F1. Linear sliding of the receptacle 1
F2. Pivoting of the sampling device 4

The invention claimed is:

1. A method for placing a receptacle having an opening and containing a liquid of interest in a device for sampling the liquid, the sampling device comprising a sampling needle, the method comprising linearly moving the receptacle and a simultaneously pivotally moving the needle, during which movements a free end of said needle is moved between a terminal position outside said receptacle and a terminal position inside it, the longitudinal axis of the needle and the perpendicular plane of the opening forming a substantially constant intersection during the placing of the receptacle.

2. The method according to claim 1, wherein the pivoting of the needle takes place in a plane containing the linear axis of movement of the receptacle.

3. The method according to claim 2, wherein the general movement of the receptacle is an upward movement, whereas the general movement of the free end of the needle is a downward movement.

4. The method as claimed in claim 2, wherein, the extreme inner position of the needle, the free end of said needle is located substantially at the lowest point of the receptacle with respect to the earth's gravity.

5. A device for sampling a liquid present in a receptacle, enabling the method for placing the receptacle to be applied, as claimed in claim 2, the device comprising:
   a sampling needle, mounted on a pivoting support, and
   a carriage supporting the receptacle, this carriage being mounted on sliding means.

6. The method according to claim 1, wherein the general movement of the receptacle is an upward movement, whereas the general movement of the free end of the needle is a downward movement.

7. The method as claimed in claim 6, wherein, the extreme inner position of the needle, the free end of said needle is located substantially at the lowest point of the receptacle with respect to the earth's gravity.

8. A device for sampling a liquid present in a receptacle, enabling the method for placing the receptacle to be applied, as claimed in claim 6, the device comprising:
   a sampling needle, mounted on a pivoting support, and
   a carriage supporting the receptacle, this carriage being mounted on sliding means.

9. The method as claimed in claim 1, wherein, in the extreme inner position of the needle, the free end of said needle is located substantially at the lowest point of the receptacle with respect to the earth's gravity.

10. A device for sampling a liquid present in a receptacle, enabling the method for placing the receptacle to be applied, as claimed in claim 4, the device comprising:
    a sampling needle, mounted on a pivoting support, and
    a carriage supporting the receptacle, this carriage being mounted on sliding means.

11. A device for sampling a liquid present in a receptacle, enabling the method for placing the receptacle to be applied, as claimed in claim 1, the device comprising:
    a sampling needle, mounted on a pivoting support, and
    a carriage supporting the receptacle, this carriage being mounted on sliding means.

12. The device as claimed in claim 11, wherein transmission means are provided between the carriage and the pivoting support.

13. The device as claimed in claim 12, wherein the transmission means comprises at least one strip comprising a guide and hinge axis.

14. The device as claimed in claim 13, wherein the sliding means comprise at least two rods parallel to each other and to the movement of the receptacle during its placing.

15. The device as claimed in claim 12, wherein the sliding means comprise at least two rods parallel to each other and to the movement of the receptacle during its placing.

16. The device as claimed in claim 11, wherein the sliding means comprises at least two rods parallel to each other and to the movement of the receptacle during its placing.

* * * * *